(12) United States Patent
Yaron et al.

(10) Patent No.: US 8,795,157 B1
(45) Date of Patent: Aug. 5, 2014

(54) METHOD AND SYSTEM FOR NAVIGATING WITHIN A COLON

(75) Inventors: Avi Yaron, Palo Alto, CA (US); Tami Frenkel, Savyon (IL)

(73) Assignee: Visionsense Ltd., Petah Tikva (IL)

( * ) Notice: Subject to any disclaimer, the term of this patent is extended or adjusted under 35 U.S.C. 154(b) by 1626 days.

(21) Appl. No.: 11/870,277

(22) Filed: Oct. 10, 2007

Related U.S. Application Data (60) Provisional application No. 60/850,837, filed on Oct. 10, 2006.

(51) Int. Cl.
*A61B 1/04* (2006.01)

(52) U.S. Cl.
USPC ........... 600/111; 600/103; 600/117; 600/118; 348/65

(58) Field of Classification Search
USPC ........... 600/103, 11, 117–118, 139, 146, 166, 600/111, 407; 345/419; 348/45, 65
See application file for complete search history.

(56) References Cited

U.S. PATENT DOCUMENTS

| | | | |
|---|---|---|---|
| 5,018,509 A * | 5/1991 | Suzuki et al. | 600/115 |
| 5,200,819 A * | 4/1993 | Nudelman et al. | 348/65 |
| 5,432,543 A * | 7/1995 | Hasegawa et al. | 348/45 |
| 5,436,655 A * | 7/1995 | Hiyama et al. | 348/45 |
| 5,613,936 A * | 3/1997 | Czarnek et al. | 600/166 |
| 5,751,341 A | 5/1998 | Chaleki et al. | |
| 5,864,359 A * | 1/1999 | Kazakevich | 348/45 |
| 5,877,803 A * | 3/1999 | Wee et al. | 348/135 |
| 6,016,439 A * | 1/2000 | Acker | 600/411 |
| 6,332,865 B1 | 12/2001 | Borody et al. | |
| 6,346,940 B1 * | 2/2002 | Fukunaga | 345/427 |
| 6,790,173 B2 | 9/2004 | Saadat et al. | |
| 6,971,990 B2 | 12/2005 | Ziegler et al. | |
| 2003/0152897 A1 * | 8/2003 | Geiger | 434/262 |
| 2005/0010082 A1 * | 1/2005 | Nishimura et al. | 600/145 |
| 2005/0151730 A1 | 7/2005 | Lobregt | |
| 2005/0168616 A1 * | 8/2005 | Rastegar et al. | 348/335 |
| 2006/0084860 A1 * | 4/2006 | Geiger et al. | 600/407 |

FOREIGN PATENT DOCUMENTS

WO WO 03/054803 7/2003

* cited by examiner

*Primary Examiner* — John P Leubecker
*Assistant Examiner* — Arnaldo Torres Diaz
(74) *Attorney, Agent, or Firm* — Merchant & Gould P.C.

(57) ABSTRACT

Method for advancing a colonoscope within a colon of the body of a patient, the method including the procedures of acquiring a stereoscopic image pair of a region of the interior of the colon, identifying topographical features in the stereoscopic image pair, determining the depth of each of the topographical features in the stereoscopic image pair, and indicating the appropriate direction to advance the colonoscope, the direction being toward at least a selected one of the topographical features with greater depth than others of the topographical features.

13 Claims, 6 Drawing Sheets

METHOD AND SYSTEM FOR NAVIGATING WITHIN A COLON

FIELD OF THE DISCLOSED TECHNIQUE

The disclosed technique relates to navigation of a medical instrument, in general, and to a method and system for advancing a colonoscope along the curves, twists, and corners of a colon in the body of a patient, in particular.

BACKGROUND OF THE DISCLOSED TECHNIQUE

The use of a colonoscope to examine the interior of the colon is known in the art. Colonoscopy is a minimally invasive endoscopic medical procedure. Colonoscopy may be used for diagnostic purposes, to identify irregularities in the colon (e.g., polyps, peptic ulcers, diverticulosis, inflammatory bowel disease, cancerous tissue, and the like), or therapeutic purposes, for treatment of such irregularities.

In general, a physician inserts the colonoscope into the colon through the anus, and then advances the colonoscope along the colon. The colonoscope includes an image detection device on a flexible tube, which provides a series of two-dimensional (2D) images of the colon interior. These images may be viewed by the physician on a display. A medical positioning system may determine the spatial position of the colonoscope with respect to a known reference system. As the physician continues to advance the colonoscope, he evaluates the acquired images to diagnose the patient.

Difficulties arise however, when attempting to navigate the colonoscope along the tortuous curves and bends of the colon. The colon is also constantly undergoing deformations and changing shape over time (e.g., stretching, contracting, twisting, and the like), further complicating the navigation of the colonoscope. The physician must occasionally adjust the direction of the colonoscope during the medical procedure, to ensure that the colonoscope remains substantially in the center of the colon interior.

U.S. Pat. No. 5,018,509 to Suzuki et al entitled "Endoscope insertion controlling apparatus", is directed to an apparatus capable of detecting endoscope insertion conditions in response to the state of the inspected object, and adapted to the automatic insertion of the endoscope. The apparatus includes an endoscope, a control apparatus, and a monitor. The control apparatus is coupled with the endoscope and with the monitor. The endoscope includes a flexible insertable part at the front, and an operating part at the rear. The insertable part includes a curvable part, an objective lens, an imaging device, a light distributing lens, and a light guide. The operating part includes an insertion driving part. The control apparatus includes a signal processing circuit, a light source apparatus, and an automatic inserting apparatus. The automatic inserting apparatus includes a plurality of divaluing circuits, a plurality of dark part extracting parts, a plurality of threshold level setting parts, a plurality of boundary extracting parts, a plurality of center extracting parts, a pattern comparing part, and a center position comparing part. The insertion driving part is coupled with the curvable part and with the automatic inserting apparatus. The signal processing circuit is coupled with the imaging device and with the monitor. The light guide is optically coupled with the light distributing lens at the front end, and with the light source apparatus at the rear end.

An operator inserts the insertable part of the endoscope into a body cavity (e.g., the large intestine). The imaging device captures an endoscope image of the body cavity. The automatic inserting apparatus receives the endoscope image. The divalued parts convert the endoscope image into a plurality of (e.g., three) divalued images, using threshold levels of brightness set by the threshold level setting parts. The dark part extracting parts extracts the dark regions corresponding to the threshold levels. The boundary extracting parts extract the boundaries of the respective regions. The center extracting parts determine the centers of the respective regions. The center position comparing part examines the respective center positions, and the automatic control apparatus determines the endoscope insertion conditions accordingly. The endoscope is inserted according to the insertion conditions. The pattern comparing part further compares the output of a dark part extracting part with a stored comparative pattern. If the pattern comparing part recognizes a pattern, it indicates that the tip of the endoscope has come too close to an inspected part (e.g., a mucous membrane). The pattern comparing part sends a signal to the insertion driving means to retract the endoscope. If the body cavity area where the endoscope is presently located is sufficiently linear, the determined center points of the respective regions will substantially coincide with one another. The endoscope progress directing means sets the progress direction toward the center points, and sets the endoscope to progress at a high speed. If the body cavity area where the endoscope is presently located is curved, the determined center points of the respective regions will lag in response to the curvature. The endoscope progress directing means sets the progress direction toward the center point representing the darkest threshold level, and sets the endoscope to progress at a medium or low speed. The signal processing circuit processes the captured image to a video signal, and sends the video signal to the monitor for displaying. The light source apparatus emits an illuminating light, which enters the insertable part via the light guide and the light distributing lens. The insertion driving part controls the advancement of the inserting part of the endoscope, such that the curvable part may be pulled in any direction. For example, angle wires are fixed to the tips of the curvable part at one end, and are pulled by a motor located in the inserting part.

U.S. Pat. No. 5,751,341 to Chaleki et al entitled "Stereoscopic endoscope system", is directed to a medical stereoscopic video endoscope system used to examine the interior of a body cavity or a hollow organ. The system includes a stereoscopic endoscope, an electronic processor module, a transmission channel, a viewing device, and a rigid tubular sheath assembly. The endoscope has a tubular barrel portion and a handle portion. The endoscope includes an objective lens system at the distal end, an optical system disposed proximal to the objective lens system, a light sensing module disposed at the proximal end, and an optical fiber. The light sensing module includes a pair of image sensors. The electronic processor module includes an image sensor control module, a video processing module, and a light source.

The objective lens system produces a left optical image and a right optical image of the examined object. The optical system transmits the left and right optical images along the endoscope toward the image sensors located in the light sensing module. The image sensors convert the two images to a pair of signals, which are transmitted to the electronic processor module via the transmission channel. The optical fiber illuminates the object with light generated by the light source.

The image sensor control module receives the signals and forwards them to the video processing module. The video processing module reformats the signals into time-multiplexed left and right image signals, and alternately provides the reformatted signals to a monitor. The monitor displays alternating left and right video images corresponding to the signals. The viewer observes the stereoscopic video images of the object on the monitor using the viewing device.

The barrel portion of the endoscope is inserted into the sheath assembly. The sheath assembly is rotatable with respect to the barrel portion. The distal tip of the sheath assembly has an angled face that rotates as the sheath assembly rotates about the barrel portion. Rotating the sheath assembly serves to change the viewing direction of the endoscope, providing additional stereoscopic viewpoints.

U.S. Pat. No. 6,332,865 to Borody et al entitled "Self-advancing endoscope", is directed to a self-advancing endoscope and a method for performing colonoscopy in humans or animals. The endoscope includes an elongated flexible tubular member, located between a distal tip at the distal end, and an external gripping portion at the proximal end. The tubular member includes an elongated channel. The elongated channel includes a piston, and a distal end adjacent to the distal tip of the endoscope. The gripping portion includes a solenoid. The solenoid is coupled to a combined frequency generator and power source external to the endoscope, and further coupled to the piston via a flexible wire.

The combined frequency generator and power source drives the solenoid to a reciprocating motion. The wire transmits the reciprocating motion of the solenoid to the piston, causing the piston to reciprocate within the elongated channel. The diameter of the piston is slightly smaller than that of the elongated channel, allowing air venting between the piston and the interior of the channel. The piston impacts the distal end of the elongated channel on each advancing stroke. The forward momentum resulting from the impact of the piston against the end wall, serves to advance the endoscope forward. The user holding the gripping portion (i.e., outside the body passage in which the endoscope is inserted) absorbs the backward momentum of the piston on each retracting stroke. The propulsion of the endoscope through the colon by "pulling" via a propulsion mechanism (i.e., the piston) at the front end, rather than "pushing" the endoscope from the rear, reduces looping of the endoscope within the colon, protecting the patient from loop-induced colon rupture.

U.S. Pat. No. 6,790,173 to Saadat et al, entitled "Shape lockable apparatus for advancing an instrument through unsupported anatomy", is directed to an apparatus and method for inserting and advancing a diagnostic or therapeutic instrument into a hollow body organ having a tortuous or unsupported anatomy, such as the esophagus or colon. The apparatus includes a handle, an overtube, a distal region having an atraumatic tip, a lumen, a Toughy-Borst valve, and an actuator. The overtube is coupled with the handle and with the distal region. The handle is coupled with the Toughy-Borst valve and with the actuator. The lumen extends from the Toughy-Borst valve at the handle through the overtube, distal region and atraumatic tip. The lumen is configured to allow passage of a colonoscope therethrough. The lumen may further allow passage of an additional diagnostic or therapeutic instrument. The Toughy-Borst valve serves to releasably lock the colonoscope to the overtube. The actuator serves to transition the overtube between a flexible state, and a rigid shape-fixed state. The atraumatic tip is deflectable by a steerable distal tip of the colonoscope.

A physician inserts the colonoscope through the lumen such that the steerable distal tip of the colonoscope is aligned with the distal region of the apparatus. The physician actuates the Toughy-Borst valve to lock the colonoscope to the overtube. The physician inserts the colonoscope and overtube into the rectum of the patient. The physician uses the steerable tip of the colonoscope to impart angular deflection to the atraumatic tip, thereby steering the tip about tortuous curves in the colon (e.g., the rectosigmoid junction). After advancing the atraumatic tip past a tortuous curve, the physician uses the actuator to lock the overtube to its current shape. The colonoscope is then advanced through the rigid overtube. When the colonoscope is advanced through the overtube, the atraumatic tip may radially expand the colon wall outwards, thereby reducing the risk that colon tissue is caught or pinched between the overtube and the colonoscope. After advancing the distal tip of the colonoscope to a further tortuous curve in the colon, the physician returns the overtube to a flexible state. The physician then advances the overtube along the colonoscope, until the overtube has also traversed the further tortuous curve. In this manner, the physician navigates the colonoscope and the overtube through the remaining tortuous curves of the colon, without distending the wall of the colon, avoiding discomfort, spasm or injury to the patient.

U.S. Pat. No. 6,971,990 to Ziegler et al, entitled "Propulsion mechanism for endoscopic systems", is directed to a propulsion apparatus for transporting accessory devices (e.g., an endoscope) within a body cavity (e.g., the colon). The apparatus includes a toroid, a frame, a series of motive rollers and suspending rollers, and a power source. The toroid includes a bladder of flexible material. The flexible material has an interior surface and an exterior surface. The interior surface defines an interior volume, which is filled with a fluid. The exterior surface defines a central cavity. The frame includes a support structure and a housing structure. The support structure is disposed inside the interior volume. The housing structure is disposed inside the central cavity. The motive rollers are is coupled with the flexible material. The power source is electrically coupled with the motive rollers (e.g., via electric motors in the housing structure). The stabilizing rollers are located on the support structure, and maintain the flexible material between them. The frame supports the flexible material. The apparatus is further coupled with an accessory tube, having a pathway which allows insertion of an accessory device, such as an endoscope.

The power source drives the motive rollers, which applies a motive directional force to the flexible material and causes the apparatus to move forward or backward. When the apparatus is in motion, the interior surface and exterior surface of the flexible material move continuously in opposite directions. As a result, the apparatus advances along its central axis, while the external flexible materials circulate around and through the frame. The exterior surface contact and conforms to the interior surface of the tubular environment (e.g., body cavity) in which the apparatus navigates. The apparatus pulls the accessory device with it, as the apparatus enters and navigates the body cavity. The toroid adapts to the curves and constrictions in the body cavity, displacing fluid when a part of the toroid is squeezed or pushed.

SUMMARY OF THE DISCLOSED TECHNIQUE

In accordance with the disclosed technique, there is thus provided a method for advancing a colonoscope within a colon of the body of a patient. The method includes the procedures of acquiring a stereoscopic image pair of a region of the interior of the colon, and identifying topographical features in the stereoscopic image pair. The method may further include the procedure of reconstructing a real-time 3D model of the colon interior from acquired stereoscopic image pairs. The method further includes the procedure of determining the depth of each identified topographical feature in the stereoscopic image pair. The method further includes a procedure of indicating the appropriate direction to advance the colonoscope, where the direction is toward at least one of the topographical features with greater depth than another of the topographical features. The method may further include the procedure of orienting the distal tip of the colonoscope in the colon toward the indicated direction.

According to the disclosed technique, there is also provided a system for advancing a colonoscope within a colon of the body of a patient. The system includes a colonoscope, a stereoscopic image acquisition device, and an image processor. The image acquisition device is disposed on the distal tip of the colonoscope. The image processor is coupled with the image acquisition device. The image acquisition device acquires a stereoscopic image pair of a region of the interior of the colon. The image processor identifies topographical features in the stereoscopic image pair, and determines the depth of each of the topographical features in the stereoscopic image pair. The image processor may reconstruct a real-time 3D model of the colon interior from acquired stereoscopic image pairs. The image processor indicates the appropriate direction to advance the colonoscope, where the direction is toward at least one of the topographical features with greater depth than another of the topographical features. The distal tip of the colonoscope is oriented in the colon toward the indicated direction.

In accordance with the disclosed technique, there is further provided a method for determining the distance advanced by a colonoscope within a colon of the body of a patient. The colonoscope advances from initial region of the colon to a successive region of the colon. The method includes the procedures of acquiring an initial stereoscopic image pair of the initial region of the colon, reconstructing an initial 3D model of the initial region according to the initial stereoscopic image pair, and identifying at least one topographical feature in the initial 3D model. The method further includes the procedure of advancing the colonoscope from the initial region of the colon to the successive region of the colon. The method further includes the procedure of acquiring a successive stereoscopic image pair of the successive region of the colon, and reconstructing a successive 3D model of the successive region according to the successive stereoscopic image pair. The method further includes the procedure of identifying the same topographical feature in the successive 3D model. The method further includes the procedure of determining the scalar distance between the initial region and the successive region by determining the distance between the distal tip of the colonoscope and the topographical feature identified in the initial 3D model, and the distance between the distal tip of the colonoscope and the same topographical feature identified in the successive 3D model.

According to the disclosed technique, there is also provided a system for determining the distance advanced by a colonoscope within a colon of the body of a patient. The colonoscope advances from initial region of the colon to a successive region of the colon. The system includes a colonoscope, a stereoscopic image acquisition device, and an image processor. The stereoscopic image acquisition device is disposed on the distal tip of the colonoscope. The image processor is coupled with the image acquisition device. The image acquisition device acquires an initial stereoscopic image pair of the initial region of the colon. The stereoscopic image acquisition device further acquires a successive stereoscopic image pair of the successive region of the colon, and reconstructing a successive 3D model of the successive region according to the successive stereoscopic image pair. The image processor reconstructs an initial 3D model of the initial region according to the initial stereoscopic image pair. The image processor identifies at least one topographical feature in the initial 3D model. The colonoscope is advanced from the initial region of the colon to a successive region of the colon. The image processor identifies at least one topographical feature in the initial 3D model. The image processor further identifies at least one topographical feature in the successive 3D model. The image processor and determines the scalar distance between the initial region of the colon and the successive region of the colon, by determining the distance between the distal tip of the colonoscope and the topographical feature identified in the initial 3D model, and the distance between the distal tip of the colonoscope and the same topographical feature identified in the successive 3D model.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

The disclosed technique overcomes the disadvantages of the prior art by providing a method and system for advancing a colonoscope along a colon, based on the depth of topographical features identified in a three-dimensional (3D) model of the colon. A stereoscopic image acquisition device, disposed on the distal tip of the colonoscope, captures stereoscopic image pairs of the interior of the colon, as the colonoscope advances through the colon. An image processor identifies various topographical features in the stereoscopic image pair, and determines the depth of each identified feature. The image processor may further reconstruct a real-time 3D model of the colon interior from the captured stereoscopic image pairs. The image processor indicates the appropriate direction to advance the colonoscope. This direction is toward at least one identified feature with greater depth than other identified features. The distal tip of the colonoscope is oriented in the colon toward the indicated direction. In the following text, the term patient refers to either the human body or the body of an animal.

Figure 1:
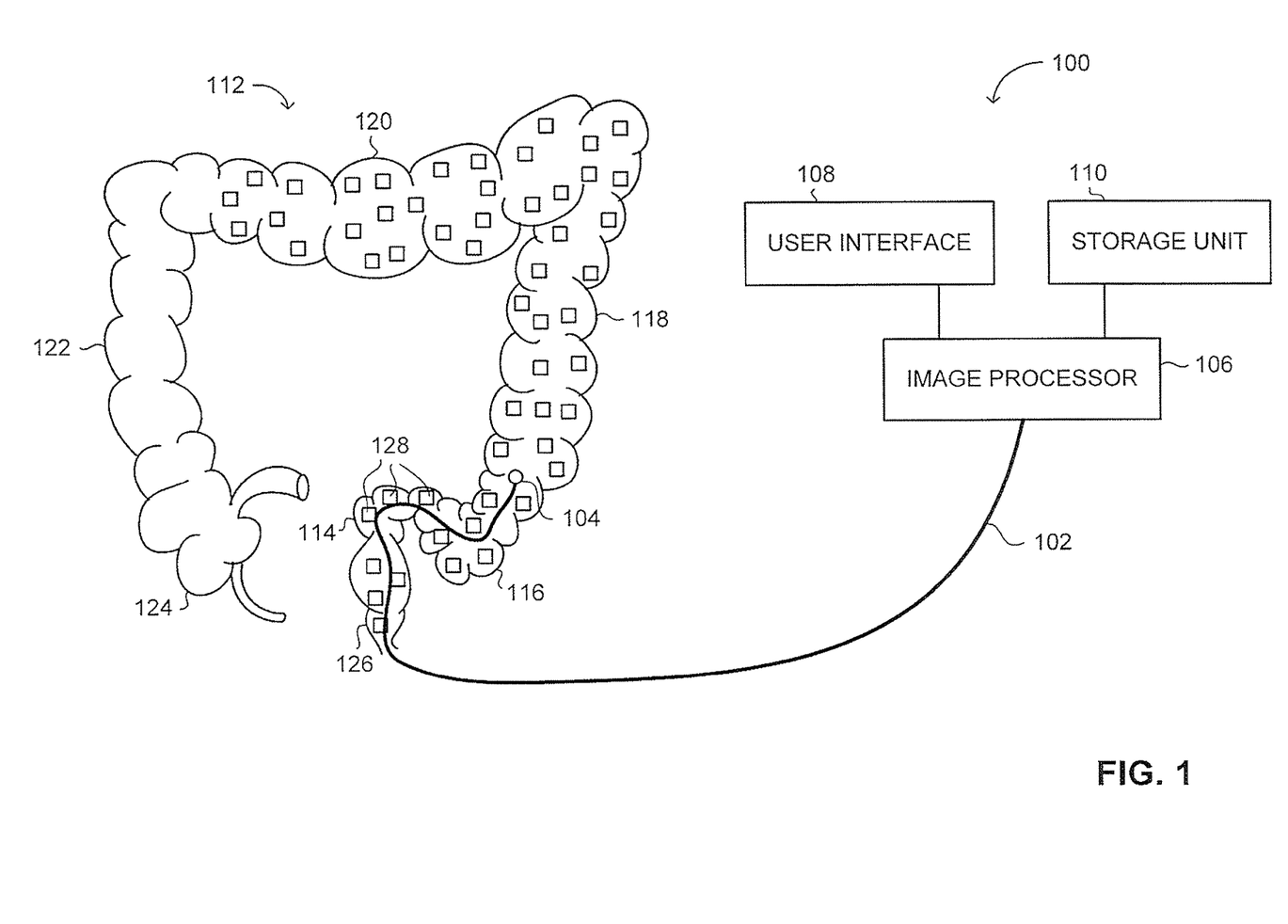
FIG. 1 is a schematic illustration of a system for advancing a colonoscope within a colon of the body of a patient, constructed and operative in accordance with an embodiment of the disclosed technique.

Reference is now made to FIG. 1, which is a schematic illustration of a system, generally referenced 100, for advancing a colonoscope within a colon of the body of a patient, constructed and operative in accordance with an embodiment of the disclosed technique. System 100 includes a colonoscope 102, a stereoscopic image acquisition device 104, an image processor 106, a user interface 108, and a storage unit 110. Stereoscopic image acquisition device 104 is disposed on the distal tip of colonoscope 102. Image processor 106 is coupled with stereoscopic image acquisition device 104, with user interface 108 and with storage unit 110.

Colonoscope 102 is inserted into a colon 112 of a body of a patient (not shown). Image acquisition device 104 is any device that is capable of capturing stereoscopic images. For example, image acquisition device 104 is a camera (e.g., operating at the visible wavelength range, the near infrared wavelength range, and the like), which captures stereoscopic images of the inner wall of colon 112. User interface 108 may be a device that provides visual feedback (e.g., a display), a device that provides audio feedback (e.g., a speaker), a device that provides tactile feedback (e.g., a haptic device), and the like.

Colon 112 includes rectum 114, sigmoid colon 116, descending colon 118, transverse colon 120, ascending colon 122, and cecum 124. Rectum 114 connects to anus 126. Rectum 114 adjoins sigmoid colon 116, which adjoins descending colon 118, which adjoins transverse colon 120, which adjoins ascending colon 122, which adjoins cecum 114. Cecum 124 connects to the small intestine (not shown) of the patient. The interior of colon 112 includes a plurality of topographical features 128 (e.g., depressions, protrusions, and the like).

A user (e.g., a physician, a medical technician, and the like) seeks to examine an area of interest located deep within colon 112, such as in transverse colon 120 or ascending colon 122. The user (not shown) inserts colonoscope 102 through anus 126 and into rectum 114. The user attempts to navigate colonoscope 102 within colon 112, into sigmoid colon 116 and beyond. As the user advances colonoscope 102 within colon 112, image acquisition device 104 continuously captures a plurality of stereoscopic image pairs of the interior of colon 112. The captured stereoscopic image pairs are stored in storage unit 110. Each stereoscopic image pair includes two two-dimensional (2D) images of the interior of colon 112, where each 2D image is viewed from different angles or viewpoints. For example, a stereoscopic image pair may include a left view 2D image and a right view 2D image. Alternatively, a stereoscopic image pair includes 2D images from a top view and a bottom view. Further alternatively, using multiple image acquisition devices for the same scene, each acquiring an image from a different perspective, different stereoscopic image pairs can be provided (e.g., left & right, top & bottom).

The user identifies various topographical features in the current stereoscopic image pair. The user determines the depth of each identified feature. Alternatively, the process of identifying features and determining the depth of each feature is automated. For example, image processor 106 determines the dimensions, and the three-dimensional location (i.e., including the depth) of each feature, via triangulation and other techniques known in the art. Image processor 106 may determine the relative depth of each identified feature (i.e., the depth of each feature in the stereoscopic image pair with respect to all the other identified features in the stereoscopic image pair).

Image processor 106 reconstructs a real-time 3D model of the interior of colon 112 based on the captured stereoscopic image pairs. The 3D model may be represented by a video image displayed on user interface 108. The 3D model provides a visual representation of the 3D location of topographical features 128 relative to one another.

Image processor 106 indicates the appropriate direction toward which colonoscope 102 should be advanced. The distal tip of colonoscope 102 is oriented in real-time, toward at least one topographical feature having greater depth than other topographical features. The adjustment of the orientation of the distal tip of colonoscope 102 may be automated. The user thereby ensures that colonoscope 102 is advanced directly through the lumen of the winding and twisting colon 112, while minimizing the possibility that the distal tip of colonoscope 102 presses against the inner walls of colon 112.

In general, the distal tip of colonoscope 102 is directed toward the most suitable (e.g. large enough to pass colonoscope 102 through) cavity or hollow space currently available, right in front of that distal tip. The orientation may be based on the location of the feature with maximum depth relative to the center of the stereoscopic image pair. For example, if the identified topographical feature with maximum depth is located substantially in the center of the stereoscopic image, the current orientation of colonoscope 102 is maintained. If the identified topographical feature with maximum depth is not located in the center of the stereoscopic image, the orientation of colonoscope 102 is adjusted toward that topographical feature. The orientation adjustment may also be based on the depth of one group of features relative to the depth of a different group of features. For example, if a group of adjacent features located on the left side of the stereoscopic image pair, have substantially greater depth than a group of adjacent features located on the right side of the stereoscopic image pair, the orientation of the distal tip of colonoscope 102 is adjusted toward the left.

Figure 2A:
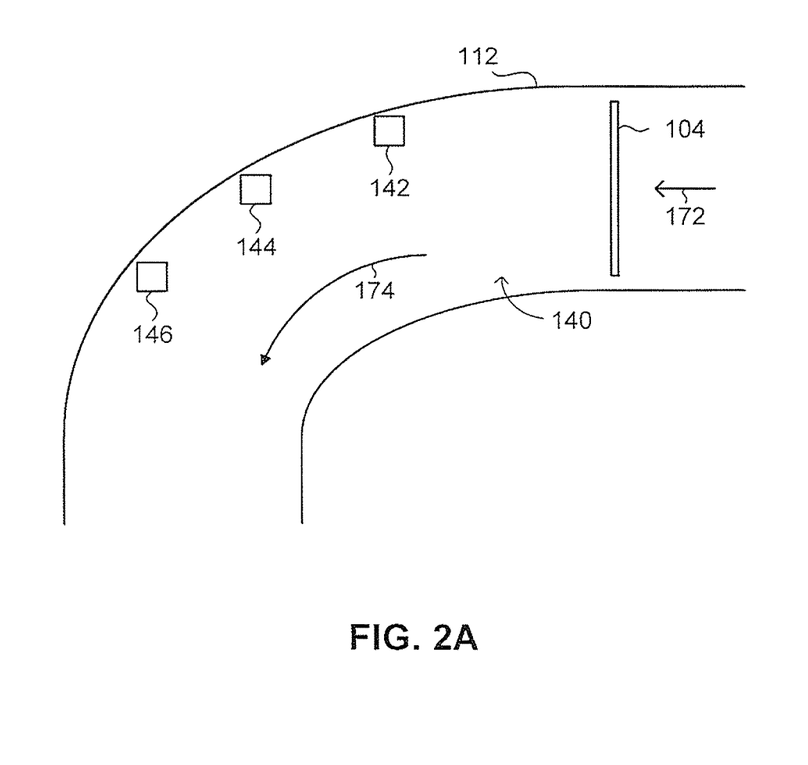
FIG. 2A is a schematic illustration in longitudinal view of an exemplary curved section of the interior of the colon of FIG. 1.
Figure 2B:
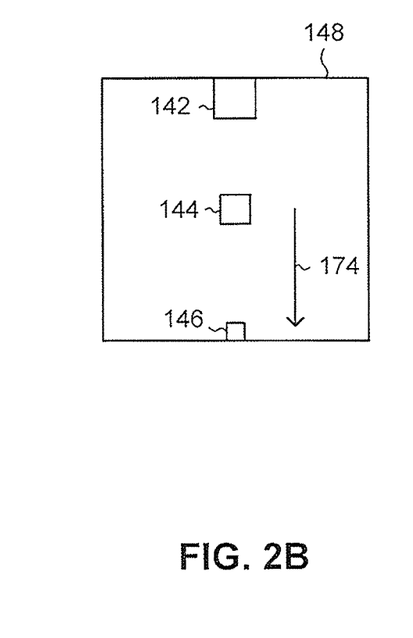
FIG. 2B is a schematic illustration in cross-sectional view of a representation of a stereoscopic image pair of the curved section of FIG. 2A, captured by the image acquisition device of FIG. 1.

Reference is now made to FIGS. 2A and 2B. FIG. 2A is a schematic illustration in longitudinal view of an exemplary curved section, referenced 140, of the interior of the colon of FIG. 1. FIG. 2B is a schematic illustration in cross-sectional view of a representation of a stereoscopic image pair, referenced 148, of the curved section of FIG. 2A, captured by the image acquisition device of FIG. 1. Section 140 of the interior of colon 112 is characterized by plurality of topographical features 142, 144 and 146. Each of topographical features 142, 144 and 146 is uniquely identifiable, and defines a unique size and location within the interior of colon 112. In section 140, topographical features 142, 144 and 146 are all substantially the same size. Image acquisition device 104 successively captures a plurality of stereoscopic image pairs of section 140. The direction of arrow 172 in FIG. 2A represents the direction in which image acquisition device 104 advances in colon 112. Image processor 106 (FIG. 1) reconstructs successive 3D models of section 140, in real-time. Each 3D model of section 140 includes the topographical features of section 140, in their appropriate relative locations.

Topographical features 142, 144 and 146 are located along a curved section 140 of colon 112, each being adjacent to an inner surface thereof. Topographical feature 144 is located deeper or further along colon 112 than topographical feature 142 (i.e., with respect to the entrance of colon 112 or anus 126). Topographical feature 146, in turn, is located deeper along colon 112 than topographical feature 144.

With reference to FIG. 2B, topographical feature 142 appears at the top of image 148, topographical feature 144 appears at the middle of image 148, and topographical feature 146 appears at the bottom of image 148. Further, topographical feature 142 appears larger than topographical feature 144, which in turn appears larger than topographical feature 146.

Image processor 106 (FIG. 1) identifies topographical features 142, 144 and 146 as representing the corresponding topographical features of section 140. Image processor 106 analyzes image 148, identifies a plurality of features in image 148, and determines the 3D location of each of the features which are identified in image 148 (i.e., via triangulation and other techniques known in the art). In particular, image processor 106 determines that topographical feature 144 is located deeper within colon 112 than topographical feature 142, and that topographical feature 146 is located deeper than topographical feature 144. Alternatively, if the size of topographical features 142, 144 and 146 are known in advance, image processor 106 may analyze a single monoscopic image (i.e., rather than a stereoscopic image pair) to determine the depth of the topographical features.

Image processor 106 determines that section 140 is substantially curved, by analyzing the corresponding 3D models (e.g., measuring the distances to the inner wall along section 140). Since topographical feature 146 is the topographical feature of section 140 having the maximum depth, and is not located at the center of image 148, image processor 106 determines that the orientation of colonoscope 102 should be adjusted toward the location of topographical feature 146. The direction of arrow 174 in FIGS. 2A and 2B represents the direction in which colonoscope 102 advances in section 140. Image processor 106 may provide an indication on user interface 108 (FIG. 1) to adjust the orientation of the distal tip of colonoscope 102 in the direction of topographical feature 146. It is noted that the entire colonoscope 102 changes configuration to adjust to the new orientation, such that once the distal tip of colonoscope 102 changes orientation, the entire colonoscope 102 follows the distal tip and advances in the new direction. The user performs the adjustment accordingly, and continues to advance colonoscope 102 beyond section 140. Alternatively, the adjustment is automated (e.g., with servos controlled by a computer). It is noted that image processor 106 performs the aforementioned processes in real-time, allowing the user to decide how to advance colonoscope 102 in real-time.

Image processor 106 may analyze the 3D model and identify a topographical feature (e.g., a polyp, cyst, tumor, diverticula, malformation, and the like) according to different properties thereof (e.g., size, shape, color). Image processor 106 may determine that a certain topographical feature requires further examination, or assist the user with various diagnostic or therapeutic procedures that may be required. Image processor 106 may further notify the user when colonoscope 102 has reached that target area of colon 112, according to the identified features.

Figure 3A:
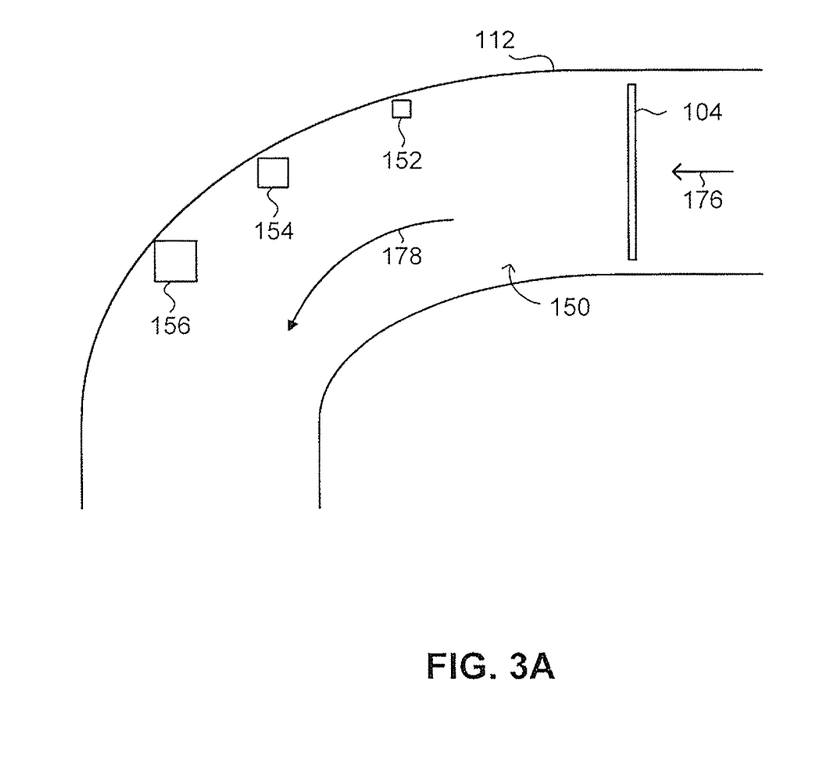
FIG. 3A is a schematic illustration in longitudinal view of another exemplary curved section of the interior of the colon of FIG. 1.
Figure 3B:
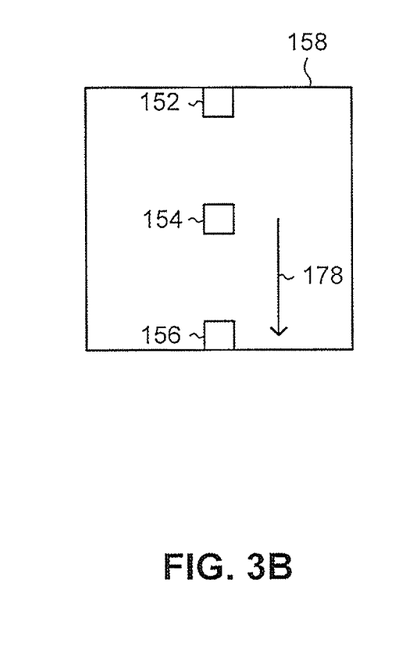
FIG. 3B is a schematic illustration in cross-sectional view of a representation of a stereoscopic image pair of the curved section of FIG. 3A, captured by the image acquisition device of FIG. 1.

Reference is now made to FIGS. 3A and 3B. FIG. 3A is a schematic illustration in longitudinal view of an exemplary curved section, referenced 150, of the interior of the colon of FIG. 1. FIG. 3B is a schematic illustration in cross-sectional view of a representation of a stereoscopic image pair, referenced 158, of the curved section of FIG. 3A, captured by the image acquisition device of FIG. 1. Section 150 of the interior of colon 112 is characterized by plurality of topographical features 152, 154 and 156. Each of topographical features 152, 154 and 156 is uniquely identifiable, and defines a unique size and location within the interior of colon 112. In section 150, topographical feature 152 is substantially smaller than topographical feature 154, and topographical feature 154 is substantially smaller than topographical feature 156. Image acquisition device 104 successively captures a plurality of stereoscopic image pairs of section 150. The direction of arrow 176 in FIG. 3A represents the direction in which colonoscope 102 advances in colon 112. Image processor 106 (FIG. 1) reconstructs successive 3D models of section 150 in real-time. Each 3D model of section 150 includes the topographical features of section 150, in their appropriate relative locations.

Topographical features 152, 154 and 156 are located adjacent to an inner surface of curved section 150. Topographical feature 154 is located further along colon 112 than topographical feature 152. Topographical feature 156, in turn, is located further along colon 112 than topographical feature 154.

With reference to FIG. 3B, topographical feature 152 appears at the top of image 158, topographical feature 154 appears at the middle of image 158, and topographical feature 156 appears at the bottom of image 158. However, in contrast to image 148 (FIG. 2B), each of topographical features 152, 154 and 156 appear substantially the same size in image 158. Although topographic feature 154 is actually larger than topographical feature 152, topographical feature 152 is nearer to image acquisition device 104 than topographical feature 154. These two effects essentially cancel each other out, resulting in each of topographical features 152 and 154 appearing substantially the same size in image 158.

Image processor 106 (FIG. 1) identifies topographical features 152, 154 and 156 as representing the corresponding topographical features of section 150. Image processor 106 analyzes image 158, identifies a plurality of features in image 158, and determines the 3D location of each of the features which are identified in image 158. In particular, image processor 106 determines that topographical feature 154 is located deeper within colon 112 than topographical feature 152, and that topographical feature 156 is located deeper than topographical feature 154.

Image processor 106 further determines that section 150 is substantially curved, by analyzing the corresponding 3D models. Since topographical feature 156 is the topographical feature of section 150 having the maximum depth, and is not located at the center of image 158, image processor 106 determines that the orientation of the distal tip of colonoscope 102 should be adjusted toward topographical feature 156. The direction of arrow 178 in FIGS. 3A and 3B represents the direction in which colonoscope 102 advances in section 150. Image processor 106 may provide an indication on user interface 108 (FIG. 1) to adjust the orientation of the distal tip of colonoscope 102 in the direction of topographical feature 156. The user performs the adjustment accordingly, and continues to advance colonoscope 102 beyond section 150.

Figure 4A:
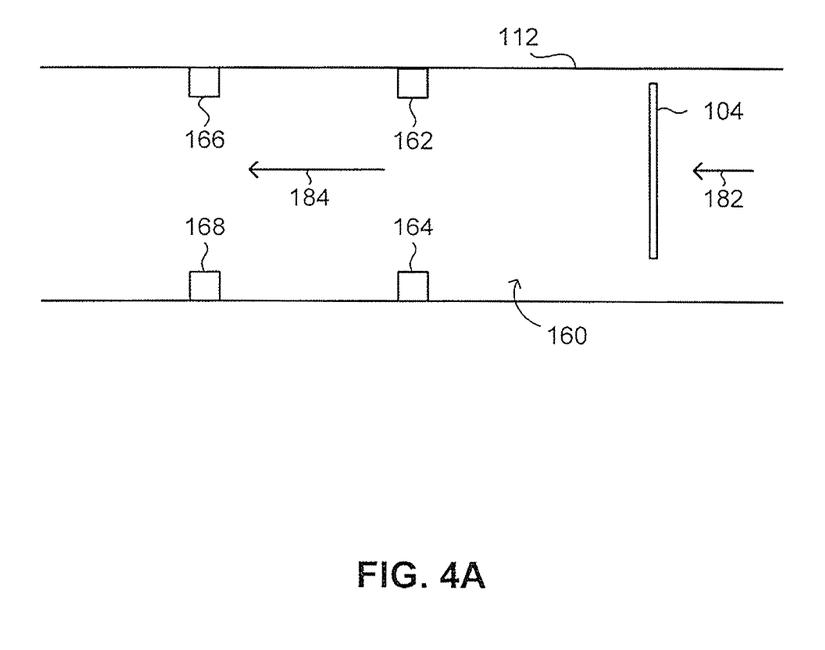
FIG. 4A is a schematic illustration in longitudinal view of an exemplary straight section of the interior of the colon of FIG. 1.
Figure 4B:
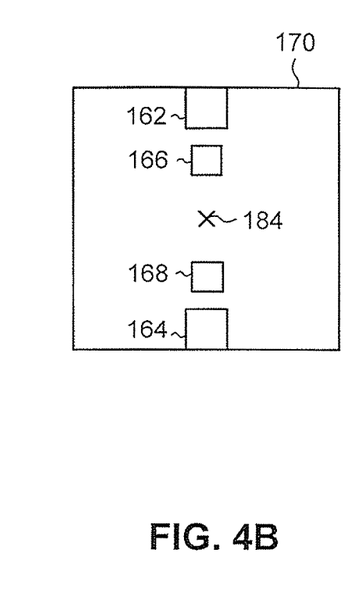
FIG. 4B is a schematic illustration in cross-sectional view of a representation of a stereoscopic image pair of the straight section of FIG. 4A, captured by the image acquisition device of FIG. 1.

Reference is now made to FIGS. 4A and 4B. FIG. 4A is a schematic illustration in longitudinal view of an exemplary straight section, referenced 160, of the interior of the colon of FIG. 1. FIG. 4B is a schematic illustration in cross-sectional view of a representation of a stereoscopic image pair, referenced 170, of the straight section of FIG. 4A, captured by the image acquisition device of FIG. 1. Section 160 of the interior of colon 112 is characterized by plurality of uniquely identifiable topographical features 162, 164, 166 and 168. In section 160, topographical features 162, 164, 166 and 168 are all substantially the same size. Image acquisition device 104 successively captures a plurality of stereoscopic images of section 160. The direction of arrow 182 in FIG. 4A represents the direction in which image acquisition device 104 advances in colon 112. Image processor 106 (FIG. 1) reconstructs successive 3D models of section 160, in real-time.

Topographical features 162, 164, 166 and 168 are located along a straight section 160 of colon 112. Topographical features 162 and 166 are located adjacent to a first inner surface of section 160, and topographical features 164 and 168 are located along the opposite inner surface. Topographical feature 166 is located further along colon 112 than topographical feature 162. Topographical feature 168 is located further along colon 112 than topographical feature 164. Topographical feature 162 is located at substantially the same depth as topographical feature 164, while topographical feature 166 is located at substantially the same depth as topographical feature 168.

With reference to FIG. 4B, topographical feature 162 appears at the top of image 170, and topographical feature 166 appears slightly below topographical feature 162. Topographical feature 164 appears at the bottom of image 170, and topographical feature 168 appears slightly above topographical feature 164. Topographical feature 162 appears larger than topographical feature 166, while topographical feature 164 appears larger than topographical feature 168.

Image processor 106 (FIG. 1) identifies topographical features 162, 164, 166 and 168 as representing the corresponding topographical features of section 160. Image processor 106 analyzes image 170, identifies a plurality of features in image 170, and determines the 3D location of each of the features which are identified in image 170. In particular, image processor 106 determines that topographical feature 166 is located deeper within colon 112 than topographical feature 162. Image processor 106 also determines that topographical feature 168 is located deeper than topographical feature 164. Image processor 106 also determines that topographical features 162 and 164 are at substantially the same depth, and that topographical features 166 and 168 are at substantially the same depth.

Image processor 106 determines that section 160 is substantially straight, by analyzing the corresponding 3D models. Image processor 106 determines that the orientation of colonoscope 102 should not be adjusted, but rather should continue according to its current direction. The user continues to advance colonoscope 102 beyond section 160, in the direction of arrow 184, maintaining the current direction of colonoscope 102.

According to another embodiment of the disclosed technique, system 100 may determine the distance traveled by colonoscope 102 within colon 112. The user advances colonoscope 102 to an initial region of colon 112, such as rectum 114. Image acquisition device 104 continuously captures a plurality of stereoscopic image pairs of the interior of rectum 114. Image processor 106 reconstructs a 3D model of rectum 114 of colon 112 (i.e., an initial 3D model) from the captured stereoscopic image pairs. Image processor 106 identifies topographical features 128 in the initial 3D model.

The user continues to advance colonoscope 102 beyond rectum 114 to a successive region of colon 112, such as sigmoid colon 116. Image acquisition device 104 continuously captures a plurality of stereoscopic image pairs of the interior of sigmoid colon 116. Image processor 106 reconstructs a 3D model of sigmoid colon 116 of colon 112 (i.e., a successive 3D model) based on the captured stereoscopic image pairs. Image processor 106 identifies topographical features 128 in the successive 3D model.

Image processor 106 examines the initial 3D model and the successive 3D model, and determines the relative distance between a topographical feature identified in the initial 3D model, and the same topographical feature identified in the successive 3D model. Image processor 106 determines the scalar distance between the initial region and the successive region of colon 112, according to the distance between the distal tip of the colonoscope and the topographical feature identified in the initial 3D model and the distance between the distal tip of the colonoscope and the same topographical feature identified in the successive 3D model. Image processor 106 thereby determines the scalar distance traveled by colonoscope 102 within colon 112, in real-time. For example, image processor 106 determines the scalar distance traveled by colonoscope from rectum 114 to sigmoid colon 116. Image processor 106 may provide an indication to the user of the scalar distance on user interface 108.

Figure 5:
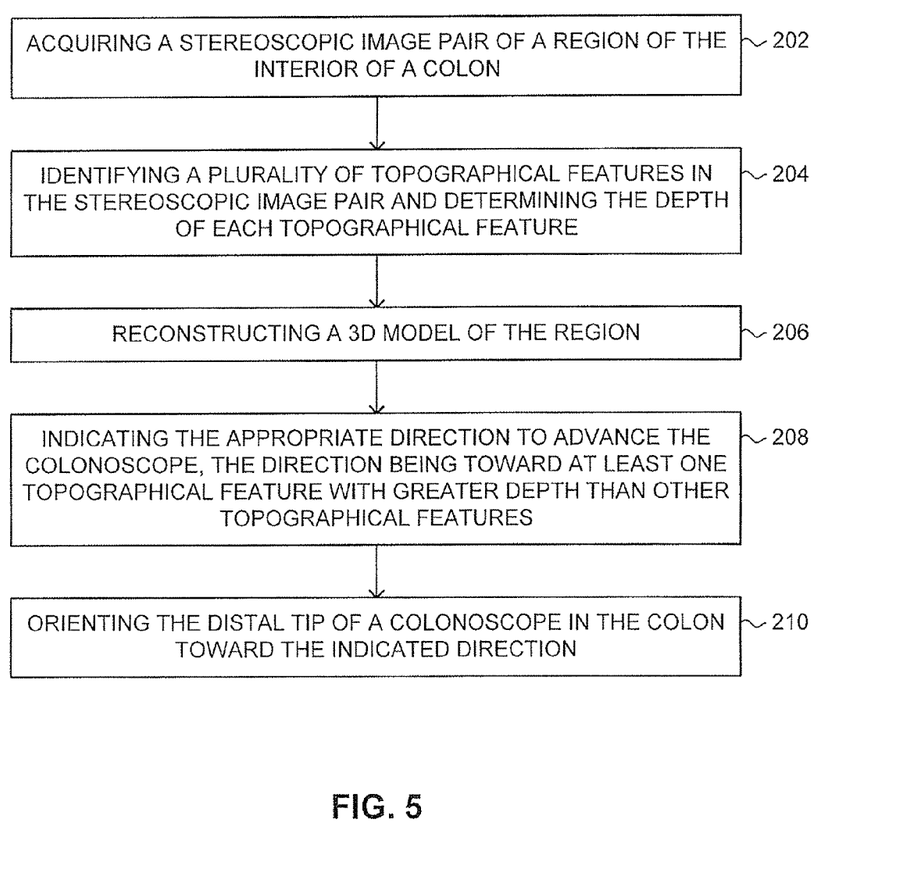
FIG. 5 is a schematic illustration of a method for advancing a colonoscope within a colon of the body of a patient, operative in accordance with another embodiment of the disclosed technique.

Reference is now made to FIG. 5, which is a schematic illustration of a method for advancing a colonoscope within a colon of the body of a patient, operative in accordance with another embodiment of the disclosed technique. In procedure 202, a stereoscopic image pair of a region of the interior of a colon is acquired. With reference to FIG. 1, stereoscopic acquisition device 104 acquires a stereoscopic image pair of a region of the interior of colon 112.

In procedure 204, a plurality of topographical features is identified in the stereoscopic image pair, and the depth of each topographical feature is determined. With reference to FIG. 1, image processor 106 identifies topographical features of colon 112 in the acquired stereoscopic image pair. Image processor 106 further determines the 3D location (i.e., including the depth) of each topographical feature.

In an optional procedure 206, a 3D model of the region is reconstructed. With reference to FIG. 1, image processor 106 reconstructs a 3D model of the region of colon 112, based on the stereoscopic image pair acquired by stereoscopic image acquisition device 104.

In procedure 208, the appropriate direction to advance the colonoscope is indicated, the direction being toward at least one topographical feature with greater depth than other topographical features. With reference to FIG. 1, image processor 106 indicates the appropriate direction toward which colonoscope 102 should be advanced. Image processor 106 may provide the indication on user interface 108. With reference to FIGS. 2A and 2B, image processor 106 determines that topographical feature 146 is the topographical feature of section 140 having the maximum depth, and that topographical feature 146 is located at the bottom of image 148. Image processor 106 directs the user to adjust the orientation of colonoscope 102 toward the location of topographical feature 146 inside colon 112. With reference to FIGS. 4A and 4B, image processor 106 determines that topographical features 166 and 168 have the maximum depth in section 160, and that topographical features 166 and 168 are located at the center of image 170. Image processor 106 directs the user not to adjust the orientation of colonoscope 102, but to continue advancing colonoscope 102 along the current direction inside colon 112.

In procedure 210, the distal tip of the colonoscope in the colon is oriented toward the indicated direction. With reference to FIG. 1, a user adjusts the orientation of the distal tip of colonoscope 102, toward the direction indicated by image processor 106. Alternatively, the adjustment of the orientation of colonoscope 102 is automated.

Figure 6:
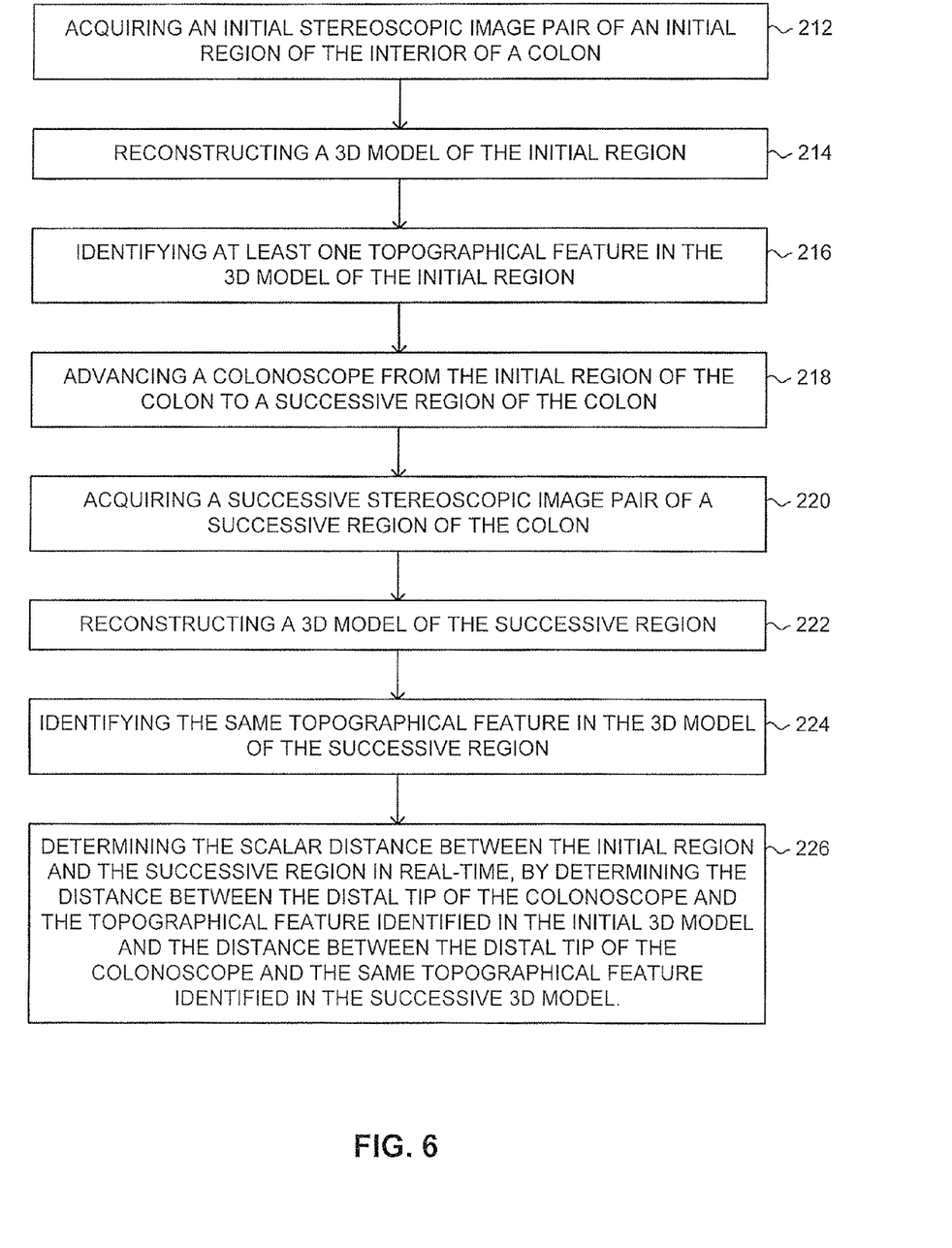
FIG. 6 is a schematic illustration of a method for determining the distance advanced by a colonoscope within a colon of the body of a patient, operative in accordance with a further embodiment of the disclosed technique.

Reference is now made to FIG. 6, which is a schematic illustration of a method for determining the distance advanced by a colonoscope within a colon of the body of a patient, operative in accordance with a further embodiment of the disclosed technique. In procedure 212, an initial stereoscopic image pair of an initial region of the interior of a colon is acquired. With reference to FIG. 1, stereoscopic image acquisition device 104 acquires an initial stereoscopic image pair of an initial region of the interior of colon 112 (e.g., rectum 114).

In procedure 214, a 3D model of the initial region is reconstructed. With reference to FIG. 1, image processor 106 reconstructs a 3D model of the initial region of colon 112, based on the initial stereoscopic image acquired by stereoscopic image acquisition device 104.

In procedure 216, at least one topographical feature is identified in the initial 3D model. With reference to FIG. 1, image processor 106 identifies topographical features of colon 112 in the reconstructed initial 3D model.

In procedure 218, a colonoscope is advanced from the initial region of the colon to a successive region of the colon. With reference to FIG. 1, a user advances colonoscope 102 from an initial region of colon 112 (e.g., rectum 114) to a successive region of colon 112 (e.g., sigmoid colon 116).

In procedure 220, a successive stereoscopic image pair of a successive region of the interior of the colon acquired. With reference to FIG. 1, stereoscopic image acquisition device 104 acquires a successive stereoscopic image pair of a successive region of the interior of colon 112 (e.g., sigmoid colon 116).

In procedure 222, a 3D model of the successive region is reconstructed. With reference to FIG. 1, image processor 106 reconstructs a 3D model of the successive region of colon 112, based on the successive stereoscopic image pair acquired by stereoscopic image acquisition device 104.

In procedure 224, the same topographical feature is identified in the successive 3D model. With reference to FIG. 1, image processor 106 identifies the same topographical feature of colon 112 in the reconstructed successive 3D model.

In procedure 226, the scalar distance between the initial region and the successive region is determined in real-time. This scalar distance is determined by determining the distance between the distal tip of the colonoscope and the topographical feature identified in the initial 3D model and the distance between the distal tip of the colonoscope and the same topographical feature identified in the successive 3D model. With reference to FIG. 1, image processor 106 determines the relative distance between a topographical feature identified in the initial 3D model, and the same topographical feature identified in the successive 3D model. Image processor 106 determines the scalar distance between the initial region and the successive region of colon 112, by determining the distance between the distal tip of the colonoscope and the topographical feature identified in the initial 3D model and the distance between the distal tip of the colonoscope and the same topographical feature identified in the successive 3D model. Image processor 106 thereby determines the scalar distance traveled by colonoscope 102 within colon 112, in real-time.

System 100 can also include an electro-magnetic position and orientation sensor, for enhancing the overall accuracy of the system, by determining the position and orientation of colonoscope 102 throughout the medical operation, relative to the body of the patient. This is achieved by adding the spatial measurements of the electro-magnetic sensor to the spatial measurements of the stereoscopic analysis.

It will be appreciated by persons skilled in the art that the disclosed technique is not limited to what has been particularly shown and described hereinabove. Rather the scope of the disclosed technique is defined only by the claims, which follow.

The invention claimed is:

1. Method for advancing a colonoscope within a colon of the body of a patient, the method comprising the procedures of:
    acquiring a stereoscopic image pair of a region of the interior of said colon,
    identifying a plurality of topographical features located on an inner wall of said colon in said stereoscopic image pair, each of said plurality of topographical features being uniquely identifiable and defining a unique size and location with the interior of said colon;
    determining the depth of each of said topographical features in said stereoscopic image pair;
    determining a radius of curvature of said colon, according to the depth of said plurality of topographical features as determined according to said stereoscopic image pair of a region of the interior of the colon; and
    advancing said colonoscope according to the direction of at least a selected one of said topographical features with greater depth than others of said topographical features and according to said radius of curvature.

2. The method according to claim 1, further comprising the procedure of orienting said colonoscope toward said indicated appropriate direction.

3. The method according to claim 2, wherein said procedure of moving is performed manually.

4. The method according to claim 2, wherein said procedure of moving is performed automatically.

5. The method according to claim 2, wherein said procedure of orienting said colonoscope comprises a sub-procedure of adjusting said colonoscope toward the location of said topographical feature having maximum depth relative to the center of said stereoscopic image pair.

6. The method according to claim 2, wherein said procedure of orienting said colonoscope comprises a sub-procedure of adjusting said colonoscope toward the location of a first group of said topographical features having greater depth than at least another group of said topographical features.

7. The method according to claim 1, further comprising the procedure of reconstructing a real-time three-dimensional (3D) model of the interior of said colon based on said acquired stereoscopic image pair.

8. The method according to claim 1, wherein said procedure of determining the depth of each of said topographical features is performed via triangulation.

9. The method according to claim 1, wherein said procedure of determining the depth of each of said topographical features, includes determining the depth of each one of said topographical features relative to others of said topographical features.

10. The method according to claim 1, further comprising a procedure of identifying at least a selected one of said topographical features, according to at least one physical topographical feature property.

11. System for advancing a colonoscope within a colon of the body of a patient, the system comprising:
    a colonoscope;
    a stereoscopic image acquisition device disposed on the distal tip of said colonoscope, said stereoscopic image acquisition device acquiring a stereoscopic image pair of a region of the interior of said colon; and
    an image processor coupled with said stereoscopic image acquisition device, said image processor identifying topographical features located on an inner wall of said colon in said stereoscopic image pair, each of said topographical features being uniquely identifiable and defining a unique size and location within the interior of said colon determining a depth for each of said topographical features in said stereoscopic image pair, said image processor determining a radius of curvature of said colon according to the depth of said plurality of topographical features as determined according to said stereoscopic image pair of a region of the interior of said colon and determining a direction of at least a selected one of said topographical features with a depth greater than the depth of others of said topographical features according to said radius of curvature.

12. The system according to claim 11, wherein said colonoscope is oriented toward said appropriate direction.

13. The system according to claim 11, further comprising a user interface coupled with said image processor, said user interface receiving an input respective of said appropriate direction.

\* \* \* \* \*